(12) United States Patent
Windahl

(10) Patent No.: US 9,110,060 B2
(45) Date of Patent: *Aug. 18, 2015

(54) AUTOMATED PACKING SYSTEM AND METHOD FOR CHROMATOGRAPHY COLUMNS

(75) Inventor: Kristian Windahl, Gustavsberg (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 1805 days.

This patent is subject to a terminal disclaimer.

(21) Appl. No.: 12/251,491

(22) Filed: Oct. 15, 2008

(65) Prior Publication Data

US 2009/0038381 A1 Feb. 12, 2009

Related U.S. Application Data

(60) Division of application No. 11/255,682, filed on Oct. 21, 2005, now Pat. No. 7,452,471, which is a continuation-in-part of application No. 11/179,925, filed on Jul. 12, 2005, now Pat. No. 7,419,599, which is a continuation-in-part of application No. 11/133,580, filed on May 20, 2005, now abandoned.

(51) Int. Cl.
*G01N 30/56* (2006.01)
*B01D 15/20* (2006.01)
*G01N 30/60* (2006.01)

(52) U.S. Cl.
CPC .............. *G01N 30/56* (2013.01); *B01D 15/206* (2013.01); *G01N 30/6021* (2013.01); *G01N 2030/565* (2013.01)

(58) Field of Classification Search
CPC . B01D 15/206; G01N 30/6021; G01N 30/56; G01N 2030/565

USPC ......... 210/635, 656, 143, 198.2, 243; 141/12, 141/73, 80
See application file for complete search history.

(56) References Cited

U.S. PATENT DOCUMENTS

| 7,419,599 B2 * | 9/2008 | Andersson et al. ........... 210/656 |
| 7,452,471 B2 * | 11/2008 | Windahl ....................... 210/656 |
| 8,137,549 B2 * | 3/2012 | Andersson et al. ........ 210/198.2 |
| 2003/0089662 A1 | 5/2003 | Hofmann |
| 2004/0016701 A1 | 1/2004 | Hauck et al. |
| 2004/0099604 A1 | 5/2004 | Hauck et al. |
| 2006/0196832 A1 | 9/2006 | Perreault et al. |
| 2006/0219616 A1 | 10/2006 | Noyes et al. |
| 2008/0272045 A1 * | 11/2008 | Andersson et al. ........ 210/198.2 |

FOREIGN PATENT DOCUMENTS

| EP | 1 336 843 | 8/2003 |
| WO | WO 02/10739 | 2/2002 |
| WO | WO 02/084275 | 10/2002 |

OTHER PUBLICATIONS

Cherrak, et al., "Behavior of packing materials is axially compressed chromatographic columns" Journal of Chromatography A, 943, 2001, 15-31.

* cited by examiner

*Primary Examiner* — Ernest G Therkorn
(74) *Attorney, Agent, or Firm* — Parks Wood LLC

(57) ABSTRACT

A column packing system comprises a control unit provided with software for monitoring the column interior pressure and/or flow through the column for use in calculating the breakpoint where a movable adapter comes into contact with a consolidated bed of bed media. The calculated breakpoint is used by the control unit to determine how much further the movable adapter has to move into the column in order to achieve a desired amount of bed compression.

4 Claims, 2 Drawing Sheets

AUTOMATED PACKING SYSTEM AND METHOD FOR CHROMATOGRAPHY COLUMNS

CROSS-REFERENCE TO RELATED APPLICATIONS

This application is a divisional of U.S. patent application Ser. No. 11/255,682 filed Oct. 21, 2005 now U.S. Pat. No. 7,452,471, which is a continuation-in-part of U.S. patent application Ser. No. 11/133,580 filed May 20, 2005, now abandoned, and to is a continuation-in-part of U.S. patent application Ser. No. 11/179,925 filed Jul. 12, 2005, now U.S. Pat. No. 7,419,599.

FIELD OF THE INVENTION

The present invention relates to a media packing system for columns and a media packing method for use in columns. More specifically, the invention relates to packing devices and methods for improving the packing of chromatography media into chromatography columns.

BACKGROUND OF THE INVENTION

Columns used in liquid chromatography typically comprise a tubular body enclosing a porous chromatography media through which a carrier liquid flows, with separation taking place by material collection between the carrier liquid and solid phase of the porous media. Typically, the porous media is enclosed in the column as a packed bed, typically formed by consolidating a suspension of discrete particles, known as slurry that is pumped or poured or sucked into the column, usually from one end. Consolidating of the slurry into a packed bed is achieved by compressing the slurry so that it is packed into a volume which is less than the volume that it would have occupied if it had sedimented under the influence of only gravity to form a sedimented bed. The efficiency of subsequent chromatographic separation relies strongly on the liquid distribution and collection system at the fluid inlet and outlet of the packed bed, and on the compression of the packed bed. If the compression of the compressed bed is too low then chromatographic separations performed on the bed suffer from "tailing". If the compression of the compressed bed is too high then chromatographic separations performed on the bed suffer from "leading". If the compression is optimum then the separation peaks formed during use exhibit neither leading nor tailing and are substantially symmetrical. The optimum degree of compression required for a column is determined experimentally for each column size (width or diameter), bed height and bed media.

Prior to any separation process, the bed has to be prepared starting from the slurry of particles that has to be introduced into the column. The process of bed formation is called 'the packing procedure' and a correctly packed bed is a critical factor influencing the performance of a column containing a packed bed. The goal of the packing procedure is to provide a bed compressed by the optimum amount of compression—the optimum compression factor. The height of the bed when it is optimally compressed is called the target compressed bed height. Large scale columns are preferably prepared by injecting into the column, through a central slurry nozzle, a predetermined volume of slurry having a specified concentration of media particles. Once the predetermined volume of slurry has been injected into the column it may be compressed by moving a movable adapter down the longitudinal axis of the column towards the bottom of the column, normally at a constant speed, e.g. 1 cm per minute. The excess liquid during this procedure is removed at the column outlet, while the particles are retained by means of a filter material, a so-called 'bed support', with pores too small to allow the particles to pass though. The packing process is complete once the packed bed has been compressed by the optimum amount. The packing process is considered as being successful if the compressed bed allows for a good and robust chromatographic performance quantified in terms of the residence time distribution over the bed. However, producing such an optimally compressed bed is not easy to achieve in practice. Bed packing has hitherto been regarded as an art rather than a science and the quality of the final packed bed is dependant on the skill of the operator controlling the filling of the column. One reason for this is that it is difficult to ensure that the actual slurry concentration fed in the column is exactly the same as the specified concentration used in the calculation of how much slurry should be fed into the column. Any difference between actual slurry concentration and the specified slurry concentration will result in the actual bed heath being different to the target bed height and/or the actual amount of compression of the bed being different from the specified compression. During filling and the subsequent packing of the column, the operator manually selects and adjusts the packing parameters such as flow rates, adapter speed of advancement and bed compression, and has to judge the point when the adapter starts compressing the bed. This point is used to calculate how much further the adapter must move in order to obtain the required amount of compression. Mistakes in the selection of any of these packing parameters may lead to a poorly performing column. It is particularly difficult to judge by eye when compression of the bed actually starts and a significant error at this point makes it impossible to obtain an optimally compressed bed.

As used herein and in the appended claims: the term "fluid system" is intended to designate the apparatus in which liquid is either introduced to or withdrawn from a cell at a zone approximately transverse the direction of flow through the cell. The term "cell" is intended to include the terms "vessel" and "column", as well as any other structure utilised by practitioners of the separation arts, to effect a separation, and/or reaction, and/or catalysation, and/or extraction of components from an admixture by bringing the admixture into contact with solid or liquid exchange media, known as the packed bed. "Cross-sectional zone" (or region or portion) refers to a region within a cell bounded by cross sections of the cell-oriented transverse (typically approximately normal) the longitudinal direction of flow through the cell. "Longitudinal direction of flow" refers to the direction of flow from an inlet towards an outlet within a cell. "Longitudinal" is used consistently to designate the dominant flow path of fluid through a cell without regard to direction. "Flow connection system" refers to a system of channels or paths that connect two points in a fluid circuit. "Distribution system" refers to structures through which fluids are introduced to a cell and "collection system" refers to structures used to collect fluids from a cell, in each instance from a cross-sectional zone.

"Sedimented bed height" refers to the height of a bed of bed media particles which is obtained when a bed of media particles is formed after the bed media particles in a slurry of a liquid and media particles in a column are allowed to sediment under the influence of gravity only—such a bed is called a "sedimented bed". "Consolidated bed height" refers to the height of a bed of bed media particles that is obtained when a bed of media particles is formed in a column while a slurry of media particles is forced to sediment under the influence of gravity and an additional downward force exerted on the bed particles, for example by the flow of fluid through the bed caused by the movement (for example, the descent) of a movable adapter towards the bed and/or liquid pumped or sucked through the bed—such a bed is called a "consolidated bed". "Compressed bed height" refers to the height of a bed of bed media particles in a column that is obtained when a consolidated bed has been compressed, for example by contact with, and further movement of, a movable adapter or the like, or by pumping fluid through the column at a higher rate than that used during consolidation of the bed—such a bed is called a "compressed bed".

SUMMARY OF THE INVENTION

The object of the invention is to provide a column packing system and a method for packing media into columns which overcomes the drawbacks of the prior art systems. Embodiments of the invention are defined in the dependent claims.

Further improvements are mentioned in the dependent claims.

One advantage with devices and methods in accordance with the present invention is that they provide beds packed to an optimum compression factor. A further advantage of such devices and methods is that they permit the reproducible and controllable packing of chromatographic columns.

DETAILED DESCRIPTION OF THE PREFERRED EMBODIMENTS

Figure 1:
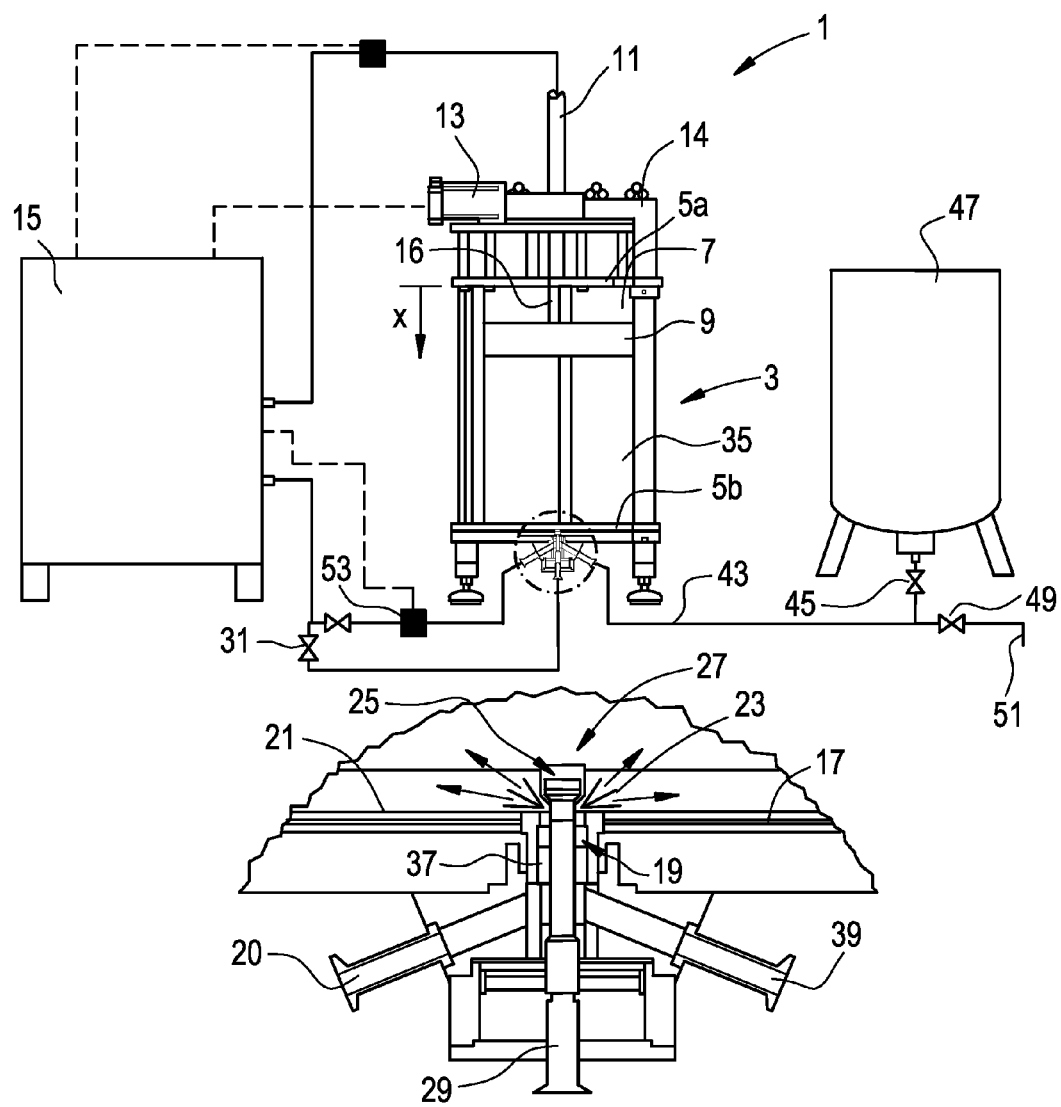
FIG. 1 shows a schematic side view of embodiments of media packing systems in accordance with the present invention.

FIG. 1 shows schematically an automated column packing system 1 in accordance with one embodiment of the present invention in which components unrelated to the present invention are omitted for ease of illustration of the principles of the present invention. System 1 comprises a column 3 which comprises upper lid or flange 5a and lower end plate 5b surrounded by a cylindrical column wall 7. Positioned between the lid or flange 5a and lower endplate 5b in column 3 is a movable adapter 9 (which may be provided with a sample distribution system, not shown, intended to distribute incoming liquid substantially evenly over the cross-section of the column 3, and a bed support, not shown, extending over the cross-section of the column with a mesh fine enough to prevent bed particles from passing through it) connected to a column inlet 11 connectable to supplies of liquids (not shown) such as sample mixtures, eluants, buffers, etc. Movable adapter 9 is movable in the longitudinal direction of the column by an actuator 13, such as a motor or piston/cylinder actuator, supported on a frame 14 passing over the upper end of the column wall 5. Movable adapter position sensing means 16 are provided to determine the position ("x") of the movable adapter relative to a fixed level, for example the upper side of the lower endplate 5b, and a signal corresponding to this distance x is send to a control unit 15. The operation of actuator 13 and the corresponding up or downwards movement of movable adapter 9 is controllable by the automated control unit 15. Control unit 15 preferably comprises hardware and software for controlling the operation of the column 3. Control unit controls the opening and closing of valves, the speed of movable adapter movement and the amount of movable adapter movement. Control unit 15 is connected to, and able to receive and record signals from, a pressure sensor 18 able to measure the pressure in the liquid inside the column—called the column interior pressure from now on for the sake of brevity.

Lower end plate 5b supports a fluid collection system 17 leading to an annular duct 19. The collection system 17 is positioned between a bed support 21 and the annular duct 19, and is intended to collect fluid evenly over the cross-section of the column and deliver it to annular duct 19. Annular duct 19 is connected to a mobile phase outlet 20 which transports the mobile phase away from the column for further processing. The bed support 21 is intended to support the weight of the bed in the column and to prevent bed media form leaving the column. The bed support 21 may, for example, be a mesh or net with apertures small enough to prevent bed media passing through the bed support. Lower endplate 5b further comprises a central aperture 23 into which a movable nozzle arrangement 25 is mountable. The nozzle arrangement comprises a cleaning-in-place (CIP) nozzle 27 connected via pipeline 29 and a remotely controllable valve 31 to for recirculating cleaning fluid in the system. Recirculation valve 31 is controllable by control unit 15. Nozzle 27 is extendable from a closed position in which it is in a leak-tight engagement with the bed support 21 and blocks central aperture 23, to an open position in which it projects through the bed support 21 into the cavity 35 of the column formed between bed support 21 and movable adapter 9. Central aperture 23 is surrounded by an annular duct 19 which is connected to a media duct 39 which is connectable to a pipeline 43 which is connectable via slurry tank valve 45 to slurry tank 47 and via drain valve 49 to a drain 51. Annular duct 19 is in fluid communication with column cavity 35 when nozzle 27 is in the open position and is blocked from fluid communication with the cavity 35 when nozzle 27 is retracted to the closed position.

In order to pack the column with bed media, the control unit is programmed with relevant media information such as the desired packed bed height (which may differ to the actual packed bed height achieved) and assumed slurry concentration, or volume of the slurry (which has a specified particle concentration which is assumed to be achieved in practice) to be fed into the column and the adapter descent speed for creating a consolidated bed, and a value representing the "compression factor"—the required amount of compression of the consolidated bed needed to give the optimum performance. The target compressed bed height can be calculated using the formula: target compressed bed height equals the consolidated bed height at the instant the adapter begins to compress the consolidated bed divided by the compression factor. For example if a consolidated bed is 1 m high when it begins to be compressed by the adapter and the compression factor is 1.15 then the target compressed bed height will be 1 m/1.15=86.96 cm high. Typically the compression factor will be within the range of 1.01-2 and is dependant, amongst others, on the column size, type and particle size of the bed media and the consolidated bed height. The predetermined volume of slurry containing bed media particles is introduced into the column, for example by suction by raising movable adapter 9 under the control of control unit 15 with slurry tank valve 45 open, nozzle 27 in the projecting open position and recirculation valve 31 closed—this causes slurry to be sucked from slurry tank 47 through slurry valve 45 along pipeline 43 through port 39 and though annular duct 19 into cavity 35. Movable adapter 9 is stopped by control unit 15 when it reaches the distance x necessary to suck the required volume of slurry into the column.

Figure 2:
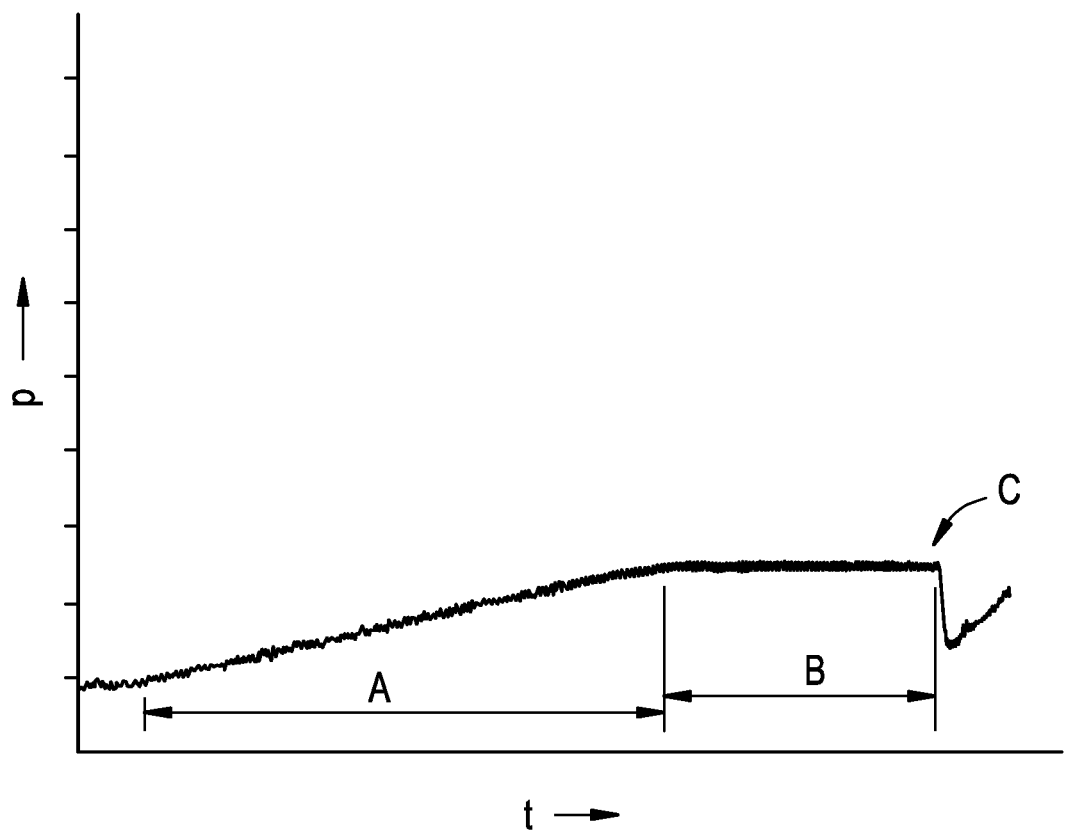
FIG. 2 shows a plot of column interior pressure against time during packing of a bed of media at constant adapter speed.

In packing mode the media valve media opening 37 is closed by retracting nozzle 27 and closing slurry tank valve 45. Mobile phase outlet 20 is opened to allow excess fluid to leave the column. Movable adapter 9 is moved down at a constant speed (e.g. between 0.5 and 10 cm per minute) and as it descends it meets the consolidated bed and starts to compress it axially—this position is called the "breakpoint". FIG. 2 shows a plot of column interior pressure against time for a column in a system in which the descent of the adapter towards the end of the column is at a constant speed. FIG. 2 shows that the descent of the adapter is characterised by a region A of steadily increasing column interior pressure (which corresponds to consolidation of the bed), followed by a region B of column interior pressure which increases less quickly or remains constant (the increase corresponding to ongoing consolidation of the bed and the constant pressure portion illustrating that no further consolidation of the bed occurs with the current adapter speed and flow through the column), followed by a sudden decrease at C in column interior pressure. This position of the adapter at the start of this sudden decrease in column interior pressure corresponds to the adapter beginning to compress the consolidated bed and is defined as being the "breakpoint". The sudden decrease is then followed by an increase in column interior pressure, this increase occurring at a higher rate than during consolidation of the bed. Control means 15 registers and monitors the signal from pressure sensor 18 and registers the position of the movable adapter where the start of the pressure decrease corresponding to the breakpoint occurs. Control means 15 calculates the distance that it is necessary to move the movable adapter from the breakpoint to achieve the desired bed compression. Control means 15 then controls the movement of movable adapter 9 so that it is moved down the distance necessary to compress the bed in order to achieve the target compressed bed height and the desired bed compression.

In a second embodiment of an automated column packing system in accordance with the present invention, the system is provided with a flow measuring device for measuring the flow rate of liquid out of the column. Such a system is substantially the same as the system described in respect of the first embodiment of the present invention apart from the pressure sensor 18 being replaced by a flow measuring device such as a flow meter 53 (shown in dashed lines in FIG. 1) positioned in a location where it can accurately measure the flow of liquid out of the column—for example in mobile phase outlet 20. This system operates in a similar way to a system in accordance with the first embodiment of the invention except that control means 15 registers and monitors the signal from flow sensor 53. Control means 15 registers the position of the movable adapter where the start of the sharp decrease in flow occurs. This decrease in flow occurs at the breakpoint. Control means 15 calculates the distance that it is necessary to move the movable adapter from the breakpoint to achieve the desired bed compression. Control means 15 then controls the movement of movable adapter 9 so that it is moved down the distance necessary to compress the bed in order to achieve the desired bed compression.

In a third embodiment of the present invention, an automated column packing system is provided with both a pressure sensor 18 and a flow measuring device 53. In this embodiment the control means 15 registers and monitors both the column interior pressure and the flow of liquid out of the column. Normally the start of the decrease in column interior pressure and the decrease in liquid flow out of the column caused by the beginning of bed compression should occur at the same time and the control means would register the position of the adapter at that time as being the breakpoint. However it is conceivable that there could be a delay in one or other of the signals from the pressure sensor or the flow measuring device such that one decrease in pressure or flow is registered before the other. In such instances the control means could be programmed to register the first detected signal showing a decrease as corresponding to the breakpoint or it could be programmed to register the second detected signal showing a decrease as corresponding to the breakpoint. As a further alternative it could be programmed to take, for example, the midpoint position of the adapter between the arrival times of the two signals showing decreases, as the breakpoint.

While the invention has been illustrated by examples of embodiments in which slurry is sucked into columns by moving the movable adapter, it is also conceivable to directly pump slurry into columns. Additionally it is also conceivable to move the adapter at non-constant speeds during consolidation of the bed and compression of the settled bed, for example starting bed consolidation at an adapter speed of e.g. 10 cm/min and lowering the adapter speed as the adapter approaches the estimated settled bed height and then continuing lowering the adapter at a slower speed e.g. 0.5 cm/min. These adapter speeds are only mentioned as illustrative examples and any suitable adapter speed may be used, for example from less than 0.5 cm/min e.g. 0.1 cm/min to more than 10 cm/min, e.g. 12.5 cm/min. Such decreases in adapter speed would, in themselves, cause decreases in pressure in or flow through a column. Additionally compression of a bed can be achieved by pumping liquid through the bed at the same time as moving the adapter towards the bed. A decrease in the flow of liquid pumped through the bed would in itself cause a decrease in the pressure in, and/or the flow through, a column. Consequently the software should be programmed to discriminate between the expected and continued decreases in flow and/or pressure caused by a decrease in adapter speed and the transient decrease in flow and/or pressure which denote the breakpoint caused by the beginning of the compression of the bed.

It is furthermore conceivable that a packing system in accordance with the present invention is provided with manual controls so that an operator is permitted to control the adapter speed during some or all of the packing procedure and the software is used to monitor the movement of the adapter and to calculate the breakpoint. The position of the calculated breakpoint, optionally with information on the calculated position of the adapter needed to achieve the desired compression factor, can be provided to the operator who then controls the movement of the adapter until it reaches the position corresponding to the desired bed compression.

The invention has been illustrated by examples of embodiments in which the column is cylindrical and has a constant diameter, thereby enabling a linear correlation between cylinder volume and bed height, it is also conceivable to adapt the present invention for application to other column shapes in which the correlation is non-linear.

Those skilled in the art, having the benefit of the teachings of the present invention as set forth above, can effect numerous modifications thereto. These modifications are to be construed as being encompassed within the scope of the present invention as set forth in the appended claims.

What is claimed is:

1. A column packing system comprising:
   a column having a longitudinal axis, a pressure sensor for sensing a column interior pressure and/or a flow measuring device for measuring liquid flow out of said column, and a movable adapter;
   said movable adapter being movable while being monitored by a control unit;

a compressing means, including automation software and hardware along the longitudinal axis of the column to compress a consolidated bed of bed media in said column to form a compressed packed bed which is compressed a predetermined amount;

wherein said control unit is provided with software for monitoring and analysing a signal from said pressure sensor and/or flow measuring device in order to determine a breakpoint when said movable adapter begins to compress said consolidated bed, wherein said movable adapter moves at a constant speed; and wherein said software is adapted to calculate the distance that said movable adapter has to move from said breakpoint to achieve the predetermined amount of bed compression and is able to control the movement of the movable adapter to a position corresponding to that distance; and said breakpoint being determined to occur when there is a decrease in the pressure inside said column and/or a decrease in the flow rate of fluid out of said column 2. The column packing system of claim 1, wherein said software is adapted to produce an operator readable signal corresponding to the position of the breakpoint.

3. The column packing system of claim 2, wherein said software is adapted to calculate the distance that said movable adapter has to move from said breakpoint to achieve the predetermined amount of bed compression and is able to produce an operator readable signal corresponding to that distance.

4. The column packing system of claim 1, wherein the column is a chromatography column and the bed includes a chromatography medium.

* * * * *